United States Patent [19]
Diamond

[11] Patent Number: 5,624,393
[45] Date of Patent: Apr. 29, 1997

[54] IRRIGATION SYSTEM FOR SURGICAL INSTRUMENTS

[76] Inventor: Eric L. Diamond, 8 Golden Grass Ct., Owings Mills, Md. 21117

[21] Appl. No.: 580,972

[22] Filed: Jan. 3, 1996

[51] Int. Cl.⁶ .................................................. A61M 31/00
[52] U.S. Cl. ............................ 604/48; 604/289; 604/290
[58] Field of Search ........................... 604/48, 49, 22, 604/289, 290; 606/167, 170

[56] References Cited

U.S. PATENT DOCUMENTS

| 3,945,375 | 3/1976 | Banko | 604/22 |
|---|---|---|---|
| 4,136,700 | 1/1979 | Broadwin et al. | 604/22 X |
| 4,562,838 | 1/1986 | Walker | 604/22 |
| 4,642,090 | 2/1987 | Utrata | 604/22 |
| 4,747,820 | 5/1988 | Hornlein et al. | 604/22 |
| 5,019,038 | 5/1991 | Linden | 604/49 |

*Primary Examiner*—John D. Yasko
*Attorney, Agent, or Firm*—Walter G. Finch

[57] ABSTRACT

The present invention provides a retrofitted attachment to an existing bone sagittal saw or drill to cool bone during the cutting and/or drilling phase of surgery. The irrigation apparatus disperses sterile fluid from an attached intravenous bag via length of slim tubing. The tubing is attached to the saw or drill and held in place by C-shaped clips. Gravity simply forces a constant flow of sterile fluid from the suspended bag to the saw blade or drill to cool the bone. Additionally, an angled jet tip directs the flow of the coolant towards the saw blade for the most beneficial effects. Finally, a thumb operated button is located at the distal end of the device to control the flow of liquid.

7 Claims, 2 Drawing Sheets

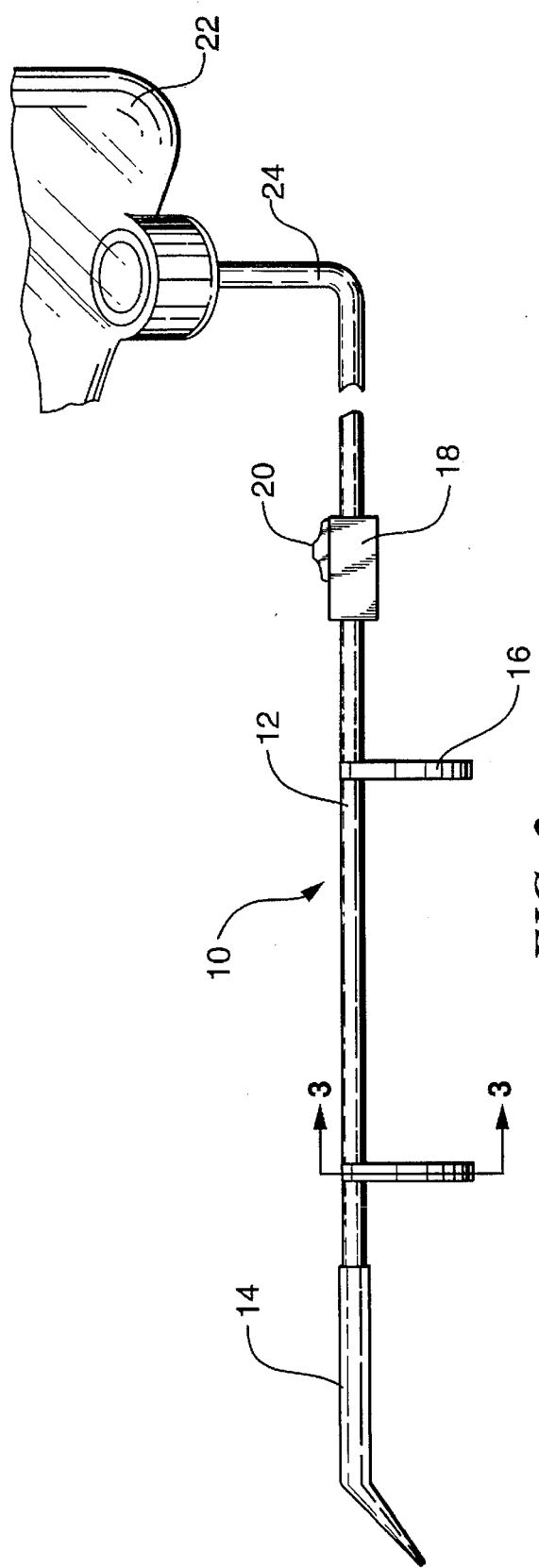
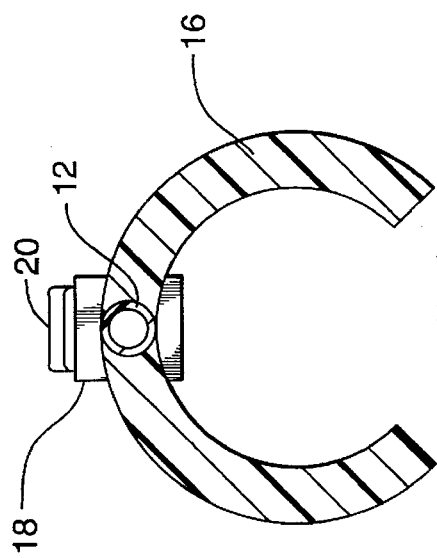
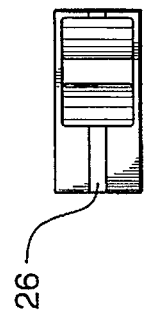
FIG. 2
FIG. 3
FIG. 4

IRRIGATION SYSTEM FOR SURGICAL INSTRUMENTS

BACKGROUND OF THE INVENTION

This invention relates to a retrofitted surgical irrigation apparatus which directs irrigating fluid at a cutting or drilling site while a medical procedure is being performed.

Generally, in any bone cutting operation, there is excessive heat production and increased temperature at the cutting site due to friction between the blade and the bone. If the heat generated by the cutting action of the saw through the bone reaches a certain level, cell death (necrosis) occurs. This can result in post surgical complications, such as reduced bone healing, inflammation, and a prolonging of the healing process.

However, the problem of heat buildup during a tissue cutting operation can be alleviated by dispersing sterile fluid at the cutting site proximal to the cutting blade. Cooling fluid directed toward the blade reduces the surgical site's temperature enough to eliminate heat induced bone necrosis and to cause a reduction in bone morbidity.

Although there are some surgical instruments in existence which address the problem of heat buildup in bone during this stage of surgery, no device available today introduces irrigation fluid via the force of gravity from an intravenous bag. Instead the other instruments use power driven applications of irrigation fluid. Use of such instruments requires purchasing expensive peripheral power supplies and irrigation units. Additionally, operating rooms which use a separate irrigation unit to irrigate the cutting site, usually require a second person to irrigate while the surgeon cuts.

Other instruments which solve the problem of cooling the cutting site incorporate an irrigation system directly into the saw blade or drill tip itself. However, these new devices require replacing the saws and drills which are currently being used with new saws and drills. This would be a costly proposition for hospitals and surgical centers.

Therefore, there is a need for a device for irrigating a surgical cutting site which is: a) passive and uses a gravitational flow; b) easily retrofitted onto existing equipment; c) compactly designed to prevent interference with regular saw function: and d) inexpensive.

SUMMARY AND OBJECTS OF THE INVENTION

The present invention provides a retrofitted attachment to an existing bone sagittal saw or drill to cool bone during the cutting and/or drilling phase of surgery. The irrigation apparatus disperses sterile fluid from an attached intravenous bag via a length of slim tubing. The tubing is attached to the saw or drill and held in place by C-shaped clips. Gravity simply forces a constant flow of sterile fluid from the suspended bag to the saw blade or drill to cool the bone. Additionally, an angled jet tip directs the flow of the coolant towards the saw blade for the most beneficial effects. Finally, a thumb operated button is located at the proximal end of the device to control the flow of liquid.

Surgeons would be benefitted by the light weight of the apparatus which prevents hand fatigue and allows utilization with one hand. In addition, the device's small size prevents it from interfering with the regular functions and controls of the saw and/or drill.

Not only is this instrument an improvement on the current devices in use, but it is cost efficient as well. The cost efficiency of the instrument stems from the fact that an new power bone cutting equipment would not have to be purchased. Instead an existing power saw could be retro fitted with the hand held irrigation unit. And since the device is so small and attaches to the primary instrument being used, the invention removes the necessity of having an assistant introduce coolant onto the cutting sites. Similarly, the device eliminates the need for additional equipment, such as a power jet lavage, since this device uses gravity to drive the fluid from the suspended intravenous bag. Finally, the device is disposable which reduces an institution's costs for re-sterilization.

Therefore, it is an object of this invention to provide an irrigation system for a bone saw or drill which is retrofitted onto an existing instrument.

It is another object of this invention to provide a surgical irrigation instrument system which can cool a bone cutting site to prevent necrosis.

It is still another object of this invention to provide a surgical instrument irrigation system which is compact and of low profile to prevent interference with the performance of a surgical procedure and operation of the saw or drill.

It is yet another object of this invention to provide a surgical instrument irrigation system which provides sterile liquid to a surgical site via the force of gravity.

BRIEF DESCRIPTION OF THE DRAWINGS

The preceding and other intended objects, features and advantages of this invention will become more readily apparent from the following description, claims and accompanying drawings in which:

FIG. 2 is a cross-sectional view along line 2—2 of FIG. 1.

DETAILED DESCRIPTION OF THE DRAWINGS

Figure 1:
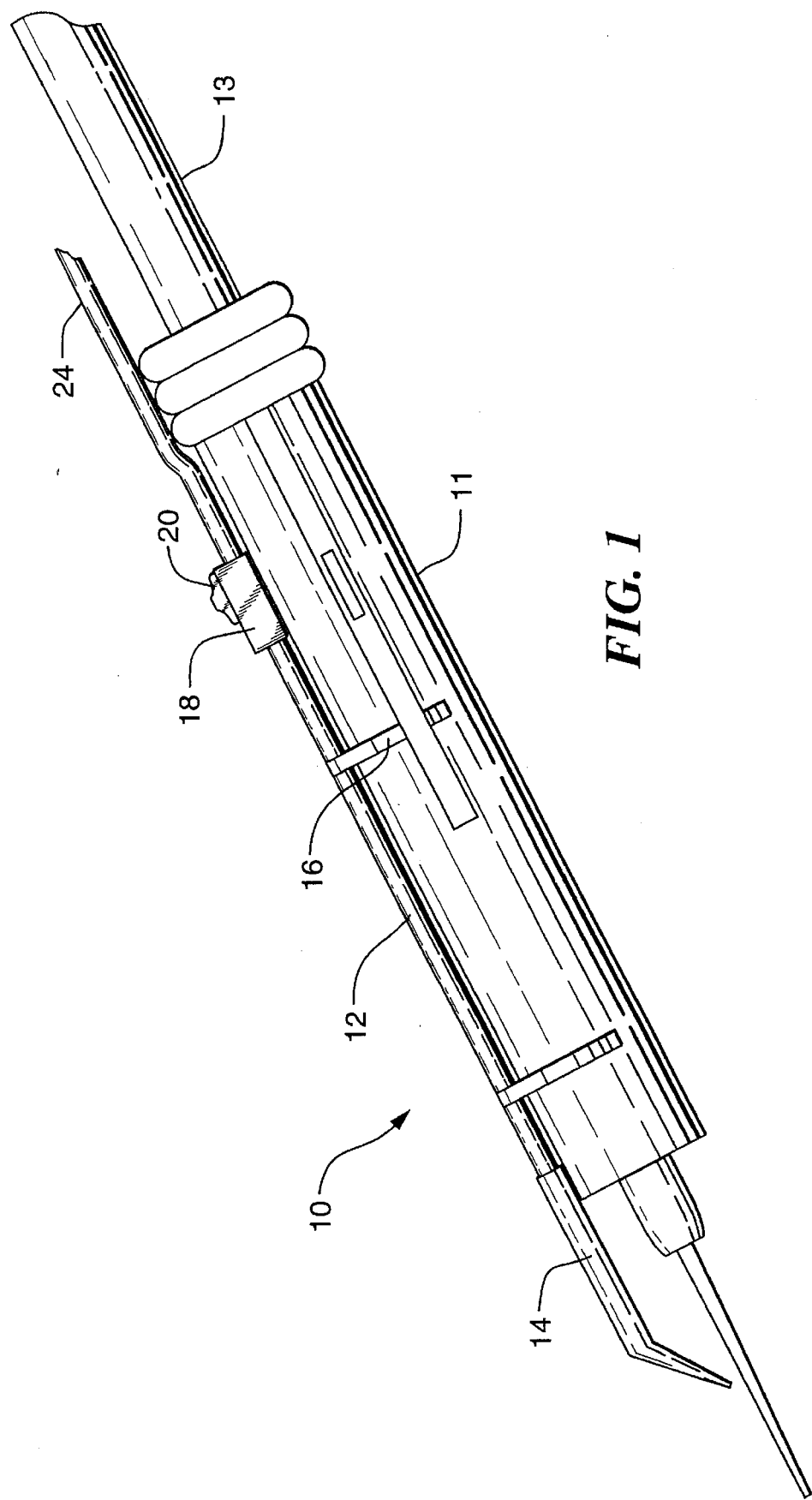
FIG. 1 is a side perspective view of the device of this invention.

Now referring to FIGS. 1 and 2, the device of the present invention is shown. The irrigation unit 10 is formed of a slim rigid tube 12. The tube is fitted with a jet nozzle 14 which is angled downward toward the blade of a surgical saw or the tip of a surgical drill. The tube 12 fits through a number of C-shaped clips 16. FIG. 1 shows two such clips 16, however one or more clips can be used without departing from the intended scope of the invention.

These clips 16 are formed of a rigid yet resilient material such as plastic. The clips 16 retrofit the irrigation unit 10 onto the handpiece of an existing bone saw or drill, as shown in FIG. 1. The clips 16 open slightly to easily fit around the saw blade or drill handle, yet are resilient enough to hold the irrigation unit 10 firmly in place. The clip 16 is shown in cross section in FIG. 2.

The tube 12 is attached to an I.V. bag holding sterile irrigation fluid via a length of flexible I.V. tubing 24. The I.V. bag is hung on an I.V. pole and the fluid is driven through the I.V. tubing 24 and the tube 12 by the force of gravity.

The sterile irrigation fluid is dispersed at the surgical site by the jet nozzle 14. The jet nozzle 14 is angled downward to direct the flow of the irrigant to the saw blade or drill tip.

The flow of the fluid is also controlled by a thumb activated valve 18. There is a button 20 which when slid forward opens the valve 18 allowing the sterile fluid to flow freely through the tube 12. When the button 20 is slid back, it closes the valve 18. The button 20 can be positioned at any point along the valve 18 to allow for a reduced, controlled flow of sterile fluid.

During a cutting operation, the water flows down the I.V. tubing 24, through the tube 12, out the jet nozzle 14 and onto the saw blade thereby cooling the blade and preventing excessive heat production. As the blades cut through the bone, the irrigation unit 10 can provide a constant supply of coolant to the cutting site.

Although the present invention has been described in considerable detail with reference to a certain preferred embodiment thereof, other embodiments are possible. For example, a different shaped clip could be employed to fit different saw or drill shapes. Furthermore, a different thumb-controlled valve could be used, such as a rotating handle, a lever or other such control well known in the art. Therefore, the spirit and scope of the appended claims should not be limited to the description of the preferred embodiment contained herein.

I claim:

1. A retrofitting irrigation system for a surgical instrument, comprising:
   a narrow tube means attached to a passive fluid source;
   a conical nozzle fitting over the outside of a portion of one end of said tube means;
   at least one resilient clip for attaching said narrow tube means to a surgical instrument; and
   valve means attached to said narrow tube means for controlling the flow of fluid from said passive fluid source through said narrow tube means to a surgical site and positioned near said resilient clip for easy manipulation by a user during surgery.

2. A retrofitting irrigation system for a surgical instrument as recited in claim 1 wherein said conical nozzle is angled to direct the flow of fluid toward a surgical site.

3. A retrofitting irrigation system for a surgical instrument as recited in claim 1 wherein said narrow tube means is formed of two connected pieces of tubing, one rigid and one flexible.

4. A retrofitting irrigation system for a surgical instrument as recited in claim 1 wherein said valve means is a thumb-operated slidable mechanism.

5. A retrofitting irrigation system for a surgical instrument as recited in claim 1 wherein said resilient clip is C-shaped for easy attachment to and removal from said surgical instrument.

6. A retrofitting irrigation system for a surgical instrument as recited in claim 1 wherein there are two resilient clips.

7. A retrofitting irrigation system for a surgical instrument, comprising:
   a narrow tube means attached to a passive fluid source, formed of two connected pieces of tubing wherein one of said pieces is rigid and the other of said pieces is flexible:
   a conical nozzle attached to one end of said tube means and angled to direct the flow of fluid to a surgical site;
   a pair resilient C-shaped clips for attaching said narrow tube means to a surgical instrument; and
   a thumb-operated slidable valve mechanism attached to said narrow tube means for controlling the flow of fluid from said passive fluid source through said narrow tube means to a surgical cutting site.

* * * * *